US00PP09254P

United States Patent [19]

Zaiger et al.

[11] Patent Number: Plant 9,254

[45] Date of Patent: Aug. 22, 1995

[54] INTERSPECIFIC TREE NAMED 'DAPPLE DANDY'

[76] Inventors: Chris F. Zaiger, 929 Grimes Ave.; Gary N. Zaiger, 1907 Elm Ave.; Leith M. Gardner, 1207 Grimes Ave.; Grant G. Zaiger, 4005 California Ave., all of Modesto, Calif. 95358

[21] Appl. No.: 345,641

[22] Filed: Nov. 28, 1994

[51] Int. Cl.[6] ..... A01H 5/00

[52] U.S. Cl. ..... Plt./38.1

[58] Field of Search ..... Plt. 38.1

*Primary Examiner*—James R. Feyrer

[57] ABSTRACT

A new and distinct variety of interspecific (plum×plum cot) tree which has the unique combination of the following desirable features:

1. Excellent flavor and eating quality.
2. Fruit having a high soluble solids, average Brix 17.4.
3. Heavy and regular production of large size fruit.
4. Vigorous upright growth.
5. Fruit with good shipping and storage quality.
6. Relatively uniform size of fruit throughout the tree.

1 Drawing Sheet

ORIGIN OF THE VARIETY

The present new and distinct variety of interspecific tree was originated by use in our experimental orchard located near Modesto, Calif., as a cross between a plum selection with the identification No. 58GA338 and a plum cot selection of unknown parentage. The plum selection with the identification No. 58GA338 originated from a cross between Laroda Plum (non-patented) and Queen Ann Plum (non-patented). A large group of seedlings were planted and grown under careful observation by us and one such seedling which represents the present variety, being especially desirable for its fruit quality was selected for asexual reproduction and commercialization.

ASEXUAL REPRODUCTION OF THE VARIETY

Asexual reproduction of the new and distinct variety of interspecific tree was reproduced by budding, as performed by us in our experimental orchard located near Modesto, Calif., which shows that all characteristics of the tree and its fruit run true to the original tree and are established and transmitted through succeeding propagations.

SUMMARY OF THE VARIETY

The new and distinct variety of interspecific tree (Plum×Plum Cot) is of large size, vigorous upright in growth and is a productive and regular bearer of large size, clingstone fruit. The fruit is further characterized as being of a relatively uniform size throughout the tree, having firm flesh with good storage and shipping quality, being excellent in flavor and eating quality and having high soluble solids (average 17.4 Brix).

DESCRIPTION OF THE PHOTOGRAPHS

The accompanying color photographs show typical specimens of the foliage and fruit of the new interspecific tree. The illustrations show the upper and lower surface of the leaves, the exterior and sectional view of the fruit divided in the suture plane to reveal flesh coloration and a stone remaining in place. The photographic illustrations were taken shortly after the fruit was picked (firm ripe) and the colors are as nearly true as is reasonably possible in a color representation of this type.

DESCRIPTION OF THE VARIETY

The following is a botanically detailed description of the new interspecific tree, its flowers, foliage and fruit, as based on observation of the specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Form.*—Upright.
- *Density.*—Medium dense.
- *Productivity.*—Productive.
- *Bearing.*—Regular.

Trunk:
- *Size.*—Large.
- *Texture.*—Medium shaggy.
- *Color.*—Grayish brown to brown (5-D-5) to (5-D-7).

Branches:
- *Size.*—Medium.
- *Texture.*—Medium rough.
- *Lenticels.*—Medium number. Medium size.
- *Color.*—Reddish brown to brown, varies with age of growth.

Leaves:
- *Size.*—Medium to large. Average length — $4\frac{3}{4}''$. Average width — $1\frac{5}{8}''$.
- *Petiole.*—Average length — 1". Medium thickness.
- *Form.*—Oblanceolate. Pointed.
- *Margin.*—Serrulate.
- *Glands.*—Globose. Size — small. Number — varies from 0 to 3. Average number 2. Located on upper portion of the petiole and base of the leaf blade.
- *Color.*—Upper surface — green to dark green (29-F-6) to (29-F-7). Lower surface — grayish green to dull green (29-E-4) to (29-E-5).

Flower buds:
- *Size.*—Medium.
- *Form.*—Plump.

*Length.*—Medium.

Flowers:

*Blooming period.*—Feb. 21, 1993 to Feb. 25, 1993. Varies slightly with climatic conditions.

*Size.*—Medium.

*Color.*—White.

*Pistil pubescence.*—Wanting.

*Pollen.*—Present.

Fruit:

*Maturity when described.*—Firm ripe.

*Date of first picking.*—Jul. 22, 1993.

*Date of last picking.*—Jul. 26, 1993.

*Size.*—Large. Average diameter axially — $2\frac{3}{4}''$. Average transversely in suture plane — $2\frac{3}{4}''$.

*Form.*—Nearly Globose, slightly larger on one side, flattened at base and apex.

*Suture.*—Shallow, extends from base to apex.

*Ventral surface.*—Nearly round, slightly flattened on the upper portion near apex.

*Cavity.*—Rounded to slightly elongated in suture plane. Average depth — $\frac{5}{8}''$. Average breadth — $\frac{3}{4}''$.

*Base.*—Retuse.

*Apex.*—Retuse, slightly flattened more on suture side.

*Stem.*—Medium length. Medium width.

Flesh:

*Ripens.*—Fairly evenly, slightly earlier nearest the apex.

*Texture.*—Firm.

*Fibers.*—Few, small, tender.

*Juice.*—Moderate.

*Aroma.*—Very slight.

*Amygdalin.*—Undetected.

*Eating quality.*—Excellent.

*Flavor.*—Excellent.

*Color.*—Varies from orange white to pale orange (5-A-2) to (5-A-3) around pit to light red to rose red (12-A-5) to (12-B-8) near skin. Pit cavity varies from dull red to brownish red (9-C-3) to (9-C-4).

Skin:

*Thickness.*—Medium.

*Texture.*—Medium, tenacious to flesh.

*Tendency to crack.*—None.

*Down.*—Wanting.

*Bloom.*—Moderate.

*Color.*—The ground color varies from tan to golden brown (5-C-b 5) to (5-C-8). Overspread with dark red to bordeaux red (11-C-8) to (11-D-8). The exposed ground color gives a randomly spaced mottled pattern.

Stone:

*Type.*—Clingstone.

*Size.*—Medium. Average length — 1″. Average breath — $\frac{5}{8}''$. Average thickness — $\frac{1}{2}''$.

*Form.*—Ovoid.

*Sides.*—Varies from equal to unequal.

*Base.*—Usually straight — varies from straight to rounded.

*Apex.*—Cuspidate.

*Surface.*—Slightly pitted throughout, ridges near base and along each side of suture vary from very slight to pronounced.

*Tendency to split.*—None.

*Color.*—Varies from light brown to brown (6-C-6) to (6-D-7).

Use: Dessert.

*Market.*—Local and long distance.

Keeping quality: Good.

Shipping quality: Good.

The interspecific tree, its flowers, foliage and fruit, herein described may vary in slight detail due to soil type, climatic conditions and cultural practices under which the variety maybe grown. The present description is that of the variety grown under the ecological conditions prevailing near Modesto, Calif.

We claim:

1. A new and distinct variety of interspecific tree, substantially as illustrated and described, characterized by its large size, vigorous upright growth and being a regular and productive bearer of large, firm, clingstone fruit with excellent flavor and eating quality; the fruit is further characterized by having high soluble solids, average Brix of 17.4, maturing relatively uniformly throughout the tree and having good shipping and storage quality.

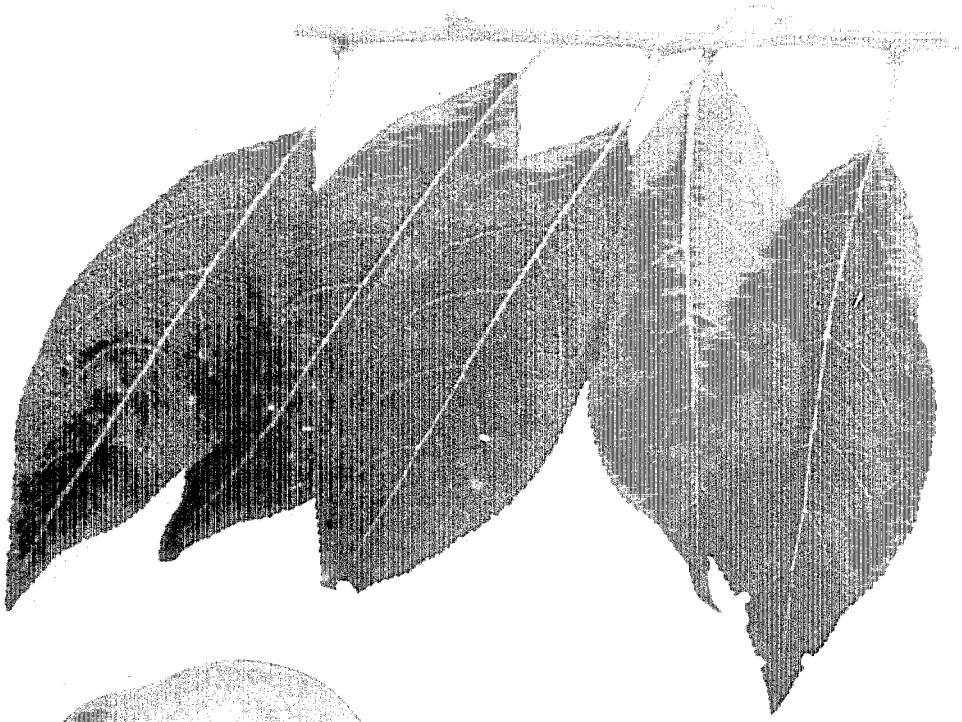
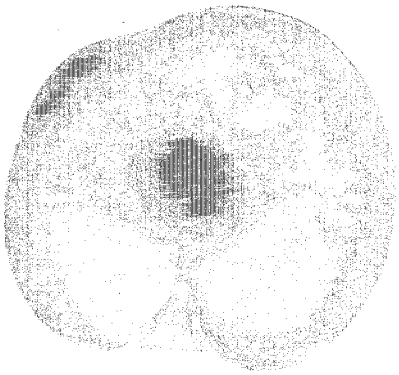
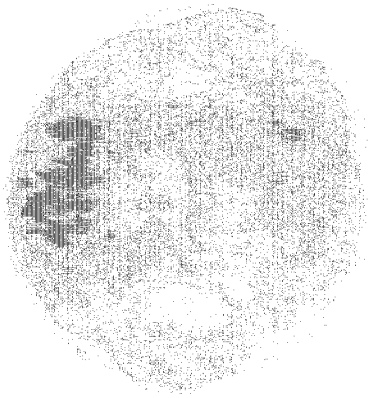
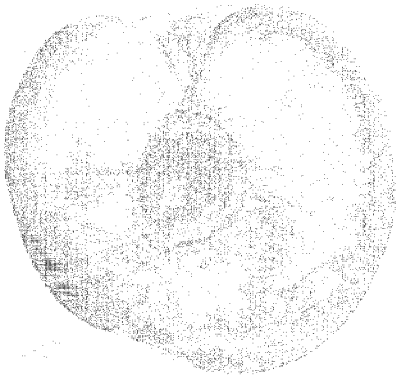
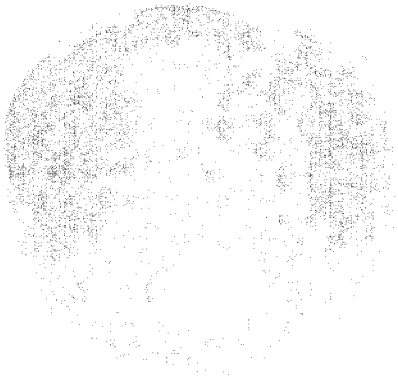

* * * * *